United States Patent [19]

Schulman et al.

[11] Patent Number: 5,324,316

[45] Date of Patent: * Jun. 28, 1994

[54] IMPLANTABLE MICROSTIMULATOR

[75] Inventors: Joseph H. Schulman, Santa Clarita, Calif.; Gerald E. Loeb, Kingston, Canada; John C. Gord, Venice; Primoz Strojnik, Granada Hills, both of Calif.

[73] Assignee: Alfred E. Mann Foundation For Scientific Research, Sylmar, Calif.

[*] Notice: The portion of the term of this patent subsequent to Mar. 16, 2010 has been disclaimed.

[21] Appl. No.: 25,889

[22] Filed: Mar. 3, 1993

Related U.S. Application Data

[63] Continuation of Ser. No. 812,136, Dec. 18, 1991, Pat. No. 5,193,539.

[51] Int. Cl.$^5$ .............................. A61N 1/36
[52] U.S. Cl. ........................ 607/61; 607/72
[58] Field of Search ............ 128/419 R, 421, 423, 128/631

[56] References Cited

U.S. PATENT DOCUMENTS

| | | | |
|---|---|---|---|
| 3,357,434 | 12/1967 | Abel | 128/419 E |
| 3,646,940 | 3/1972 | Timm et al. | 128/421 |
| 3,667,477 | 6/1972 | Susset et al. | 128/419 E |
| 3,727,616 | 4/1973 | Lenzkes | 128/419 E |
| 3,842,841 | 10/1974 | Brighton et al. | 128/419 F |
| 3,870,051 | 3/1975 | Brindley | 128/419 E |
| 4,006,748 | 2/1977 | Schulman | 128/419 P |
| 4,313,438 | 2/1982 | Greatbatch | 128/419 F |
| 4,333,072 | 6/1982 | Beigel | 340/825.54 |
| 4,333,469 | 6/1982 | Jeffcoat et al. | 128/419 F |
| 4,357,497 | 11/1982 | Hochmair | 128/420.6 |
| 4,440,178 | 4/1984 | Bussard et al. | 128/784 |
| 4,494,545 | 1/1985 | Scocum et al. | 128/419 P |
| 4,524,774 | 6/1985 | Hildebrandt | 128/421 |
| 4,599,546 | 10/1985 | Kelly et al. | 128/419 F |
| 4,611,597 | 9/1986 | Kraus | 128/419 F |
| 4,628,933 | 12/1986 | Michelson | 128/419 R |
| 4,654,880 | 3/1987 | Sontag | 128/420.6 |
| 4,665,896 | 5/1987 | LaForge et al. | 128/419 F |
| 4,679,560 | 7/1987 | Galbraith | 128/419 R |
| 4,739,764 | 4/1988 | Lu et al. | 128/419 R |
| 4,763,656 | 8/1988 | Nauman | 128/421 |
| 4,785,827 | 11/1988 | Fischer | 128/420 |
| 4,934,368 | 6/1990 | Lynch | 128/419 R |
| 4,991,582 | 2/1991 | Byers et al. | 128/419 R |
| 5,094,242 | 3/1992 | Gleason et al. | 128/422 |
| 5,105,811 | 4/1992 | Kuzma | 128/420.6 |

OTHER PUBLICATIONS

Guyton et al., "Medical & Biological Engineering", Sep. 1974, pp. 613-619.
Hildebrandt et al. "Proc. 7th International Symposium on External Control of Human Extremities", Yugoslauk 7-12 Sep. 1981 pp. 2-15.
Becker, "Bulletin of the N.Y. Academy of Sciences", vol. 48, No. 4 May 1972, pp. 627-641.
Robblee et al. "Journal of Electrochemical Society" vol. 130, No. 3, Mar. 1983, pp. 731-733.
Lazimierczok et al., "IEEE Transactions on Circuits and Systems", vol. CAS34, No. 2, Feb. 1987 pp. 149-158.
Rose et al., "Journal of Neuroscience Methods", vol. 12 1985, pp. 181-193.
Unknown Author, "CRC Critical Reviews in Bioengineering" Sep. 1981, pp. 77-79 incomplete.
Specification Sheet, Identification Deukes Inc.-No Other Information Available.
Heetderks "IEEE Transactions on Biomedical Engineering", vol. 35, No. 5, May, 1988.

Primary Examiner—William E. Kamm
Attorney, Agent, or Firm—Fitch, Even, Tabin & Flannery

[57] ABSTRACT

An addressable, implantable microstimulator is substantially encapsulated within a hermetically-sealed housing inert to body fluids, and of a size and shape capable of implantation in a living body, by expulsion through a hypodermic needle. Power and information for operating the microstimulator is received through a modulated, alternating magnetic field in which a coil is adapted to function as the secondary winding of a transformer. Electrical energy is stored in capacitor means and is released into the living body by controlled, stimulating pulses which pass through body fluids and tissue between the exposed electrodes of the microstimulator. Detection and decoding means within the microstimulator are provided for controlling the stimulating pulses in accordance with the modulation of the received, alternating magnetic field. Means for controllably recharging the capacitor is provided.

40 Claims, 9 Drawing Sheets

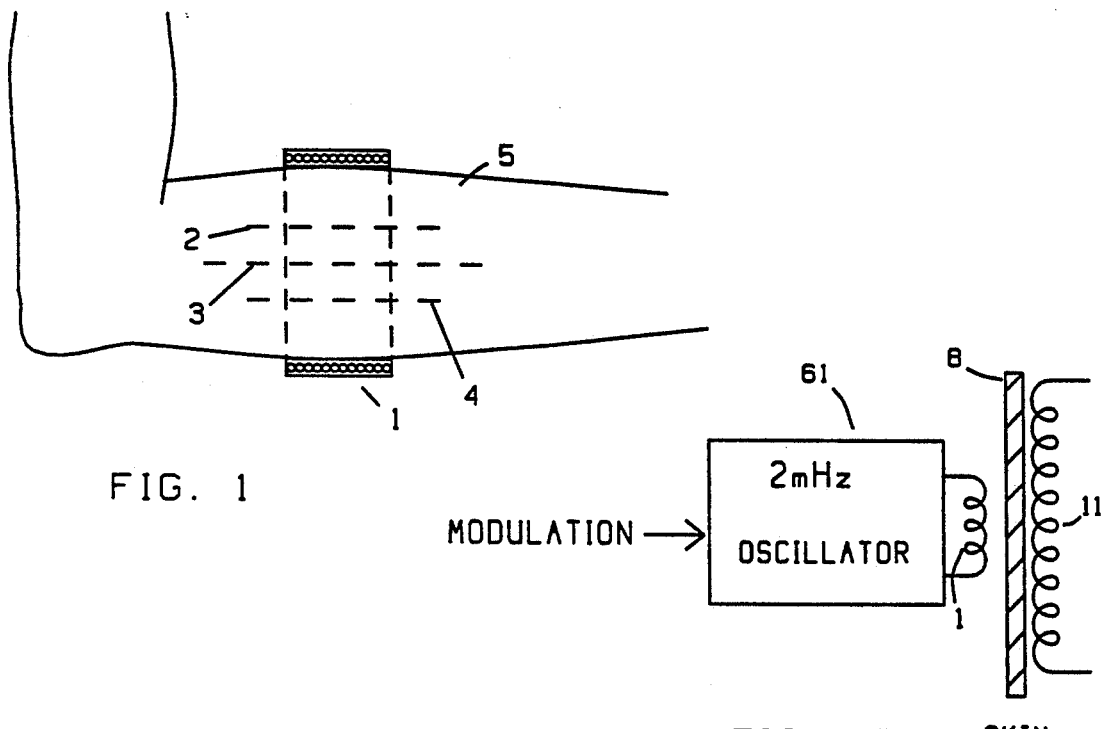
FIG. 1
FIG. 10
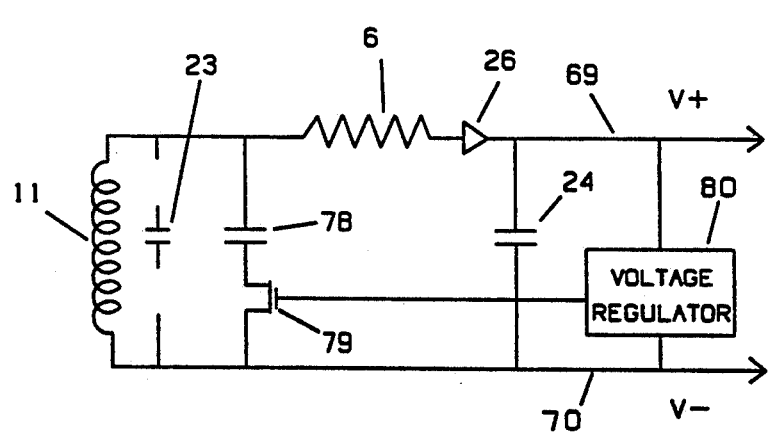
FIG. 11

IMPLANTABLE MICROSTIMULATOR

This invention was made with Government support under Contract No. NO1-NS-9-2327, awarded by the National Institutes of Health. The Government has certain rights in this invention.

This is a continuation of application Ser. No. 812,136, filed 18 Dec. 1991 and now U.S. Pat. No. 5,193,539.

This invention relates to a microstimulator for implantation in a living body, in the immediate vicinity of tissue, fluids or other body cells which are to be electrically stimulated. It is of a size and shape capable of implantation by expulsion through the lumen of a hypodermic needle. It is substantially encapsulated within a hermetically-sealed housing which is inert to body fluids and provides exposed electrodes for electrically-stimulating the desired body cells, whether muscle, nerve, receptor, gland or other area or organ of the body.

This application relates to three other patent applications filed on or about the same date as this application, entitled STRUCTURE AND METHOD OF MANUFACTURE OF AN IMPLANTABLE MICROSTIMULATOR, invented by the same inventors as herein, IMPLANTABLE DEVICE HAVING AN ELECTROLYTIC STORAGE ELECTRODE invented by one of the inventors herein, Gerald E. Loeb, and IMPLANTABLE MINIATURE COMMUNICATOR AND SENSOR MEANS invented by two of the inventors herein, Joseph H. Schulman and Gerald E. Loeb.

BACKGROUND

Neurological disorders are often caused by neural impulses failing to reach their natural destination in otherwise functional body systems. Local nerves and muscles may function, but, for various reasons, such as injury, stroke, or other cause, the stimulating nerve signals do not reach their natural destination. For example, paraplegics and quadraplegics have intact nerves and muscles and only lack the brain to nerve link, which stimulates the muscles into action.

Prosthetic devices have been used for some time to provide electrical stimulation to excite muscle, nerve or other cells. Such devices have ranged in size and complexity from large, bulky systems feeding electrical pulses by conductors extending through the skin, to implanted stimulators which are controlled through high-frequency, telemetry signals, which are modulated rf signals, such as set forth in U.S. Pat. No. 4,524,774, Apparatus and Method for the Stimulation of a Human Muscle, invented by Jurges Hildebrandt, issued Jun. 25, 1985. The use of frequencies of 27.12 MHz and 40.6867 MHz are there mentioned. Other devices have comprised a centrally-implanted stimulator package sending stimulation signals to a multitude of distant target sites.

Complications, including the possibility of infection, arise in the use of stimulators which have conductors extending through the skin. On the other hand, in the use of implanted stimulators, difficulties arise in providing suitable, operable stimulators which are small in size and in passing sufficient energy and control information to the stimulators, without direct connection, to satisfactorily operate them without direct connection.

The device of the invention uses a source of electrical energy, modulated by desired control information, to selectively control and drive numerous, small stimulators disposed at various locations within the body. Thus, for example, a desired, progressive muscular stimulation may be achieved through the successive or simultaneous stimulation of numerous stimulators, directed by a single source of information and energy outside the body.

The appropriate, functioning design of a suitable, small stimulator, a microstimulator, which can be easily implanted, such as by expulsion through a hypodermic needle, is difficult to achieve. Notwithstanding the small size, the microstimulator must be capable of receiving and storing sufficient energy to provide the desired stimulating pulses, but also, may be required to respond to received control information as to pulse duration, current amplitude and shape. Further, stimulators should achieve a "charge balancing", that is, a balancing of current flow through the body tissue in both directions to prevent damage to the tissue which results from continued, preponderance of current flow in one direction.

Also in providing the "charge balancing", it must be assured that the current flow in the opposite direction from the stimulation pulse does not cause damage to the intermediate body cells or cause undesired stimulation. Further, the "charge balancing" must not cause anodic or cathodic deterioration of the stimulating electrodes.

SUMMARY OF THE INVENTION

This invention teaches the electrical elements of an implantable, microstimulator useful in a wide variety of applications. Others have proposed microstimulators and have suggested constructing them, but none have taught all the elements set forth herein for successful construction and operation of the microstimulator.

The device of the invention is a very small stimulator and can be easily implanted, such as by expulsion through a hypodermic needle. It is operable to provide stimulation pulses of desired duration, desired current amplitude and desired shape. The stimulation pulses are delivered to the body through electrodes exposed on the outer surface of the microstimulator. Within the microstimulator, an induction coil receives energy from outside the body and a capacitor is used to store electrical energy which is released to the microstimulator's exposed electrodes under the control of electronic control circuitry means. The body fluids and tissue between the exposed electrodes provide the electrical path for the stimulating pulse. The capacitor is controllably recharged, using the same exposed electrodes and using the same body fluids and tissue path, to achieve "charge balancing". Microelectronics are included within the microstimulator to provide the electronic control circuitry for controlling the various functions.

The microstimulator of this invention receives both energy and control information from a modulated, alternating magnetic field. A coil, acting as a secondary winding of a transformer, receives the alternating magnetic field energy which is rectified and stored on a capacitor. Regulation of the charge on the capacitor is provided. Electronic control means detects and decodes the modulating information to provide the desired control. Such control includes validating the received information, providing the stimulation signal, (its duration, amplitude and shape), and controlling the recharge of the capacitor for the stimulating charge.

It is, therefore, an object of this invention to provide a microstimulator of a size and shape capable of implantation by expulsion through a hypodermic needle.

It is another object of this invention to provide a microstimulator which receives and utilizes an alternating magnetic field as a source of power.

Another object of this invention is to provide a microstimulator which receives a modulated, alternating magnetic field and detects the modulation to control a stimulating pulse.

A further object of this invention is to provide a microstimulator which effectively detects and demodulates the received, control signals.

Still another object of this invention is to provide a microstimulator in which the stimulating pulse duration, pulse amplitude and pulse shape are controlled by a received alternating magnetic field.

A final object of this invention is to provide a microstimulator in which energy is controllably stored in capacitor means, controllably discharged as a stimulating pulse and which is controllably recharged to provide "charge balancing" and to prevent undesired stimulation and damage to the body.

DESCRIPTION OF THE DRAWINGS

Further objects and features will be apparent from the following description and drawings in which:

FIG. 1 is an overall view of the device of the invention as applied to an arm, showing the primary coil in cross-section and a representation of a number of microstimulators implanted in the arm.

FIG. 10 shows a driving circuit comprised of a modulated 2 mHz oscillator, a transmitter coil and an implanted receiver coil;

FIG. 11 is an alternate embodiment for controlling the amount of energy received and stored by the microstimulator;

DETAILED DESCRIPTION OF THE INVENTION

The microstimulator of the invention is on the order of 2 mm in diameter and 10 mm long. Because of such diminutive character, it is readily implanted in a living person or animal through the lumen of the needle of a hypodermic syringe. The technique for implanting the microstimulator is to inject the point of the needle of the hypodermic syringe to the desired location for the microstimulator and to withdraw the needle while compressing the plunger of the syringe, to expel the microstimulator and leave it in place as the syringe needle is withdrawn.

Because of the small size of the microstimulator, it has been difficult to establish its parameters in order to obtain the desired operating characteristics. The following description sets forth suitable, working parameters for constructing and operating such a microstimulator.

FIG. 1 shows, figuratively, how a primary coil 1, which produces an alternating magnetic field, at a frequency, say, of 2 mHz, is disposed with respect to a number of microstimulators such as 2, 3, and 4, implanted, say, in an arm 5. The microstimulators, of course, may be planted in or near any part of the body, in the brain, a muscle, nerve, organ or other body area. The system operates as an air-gap transformer in which coil 1 is the primary winding, exterior to the body, and the microstimulators such as 2, 3 and 4 each have coils within them which act as secondary windings of the transformer.

Coil 1, for example, may be 12 to 20 turns of #200/38 Litz wire, and wound 20 cm long and 9 cm in diameter for operation with, for example, 256 microstimulators implanted in an arm. The current flowing in such coil 1 may be from less than an ampere to several amperes. A preferred embodiment uses less than 1 ampere. If the transmitting coil 1 and its associated capacitors, not shown, in FIG. 10, are tuned to resonance at the alternating frequency, little power would be lost in the transmission process.

Each microstimulator has its own identifying address and, therefore, is individually addressable. The number of microstimulators which may be actuated is therefore determined, as a practical matter, by the number of address bits available for distinguishing the individual microstimulators. Eight address bits would provide 256 different addresses for a similar number of microstimulators. Of course, a plurality of microstimulators may be assigned the same address in applications where simultaneous stimulation by more than one stimulator would be desired.

Alternatively, in FIG. 1, coil 1 may be a pancake type coil or a saddle-type coil and disposed on the surface of the skin and not necessarily entirely encompass a limb or other body part. It may not, in such case, be as efficient in transferring energy to the microstimulators.

Figure 2:
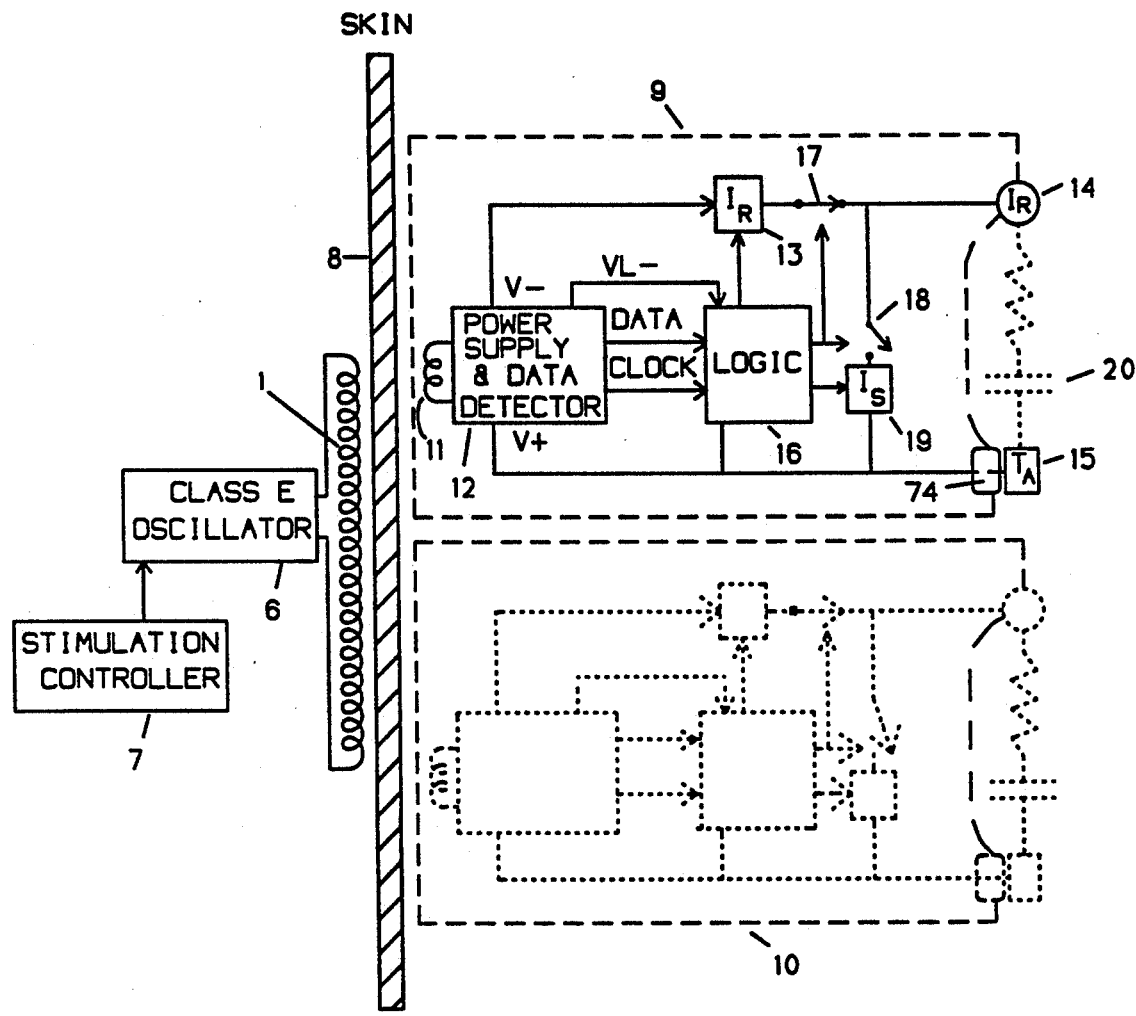
FIG. 2 is block diagram illustrating the transcutaneous transmission of power and information to implanted microstimulators.

FIG. 2 is a block diagram illustrating the transcutaneous transmission of power and information to implanted microstimulators. It shows a modulated, power source on the left, the skin and two implanted microstimulators on the right. Coil 1 is driven by a modulated oscillator 6 which, in turn, is driven by a stimulation controller 7. Underneath (shown to the right of) skin 8 are implanted microstimulators such as 9 and 10. Microstimulator 9 is shown in greater detail. Secondary coil 11, within microstimulator 9 receives energy and control information from the modulated, alternating magnetic field provided by coil 1 and passes such energy and information to electronic control means which comprises power supply and data detector 12 which, in turn, provides power to an electrode recharge current controller 13 and stimulating electrodes 14 and 15. The recharge current, or "current balancing", may be on the order of 1 per cent of the stimulating current in order to avoid undesired stimulation, damage to the body and electrode deterioration.

FIG. 2 shows secondary coil 11 at or near the surface of the skin. Such is for illustration only. The microstimulator may be much deeper, at any desired location within the arm, along the length of the transmitting coil 1, FIG. 1 and, even, for some distance beyond the ends of the coil 1. In one experimental determination, it was found that the microstimulators may lie as far as about 5 cm. outside the volume encompassed by coil 1.

Electrode 14, in the preferred embodiment, comprises an iridium ball having a stem extending into the microstimulator. The iridium ball and stem are formed by melting a 0.006" or 0.010" iridium wire such that it forms a ball at the end of the wire. A substantial portion of the iridium ball is exposed outside the stimulator and is activated. See FIG. 8.

Figure 8:
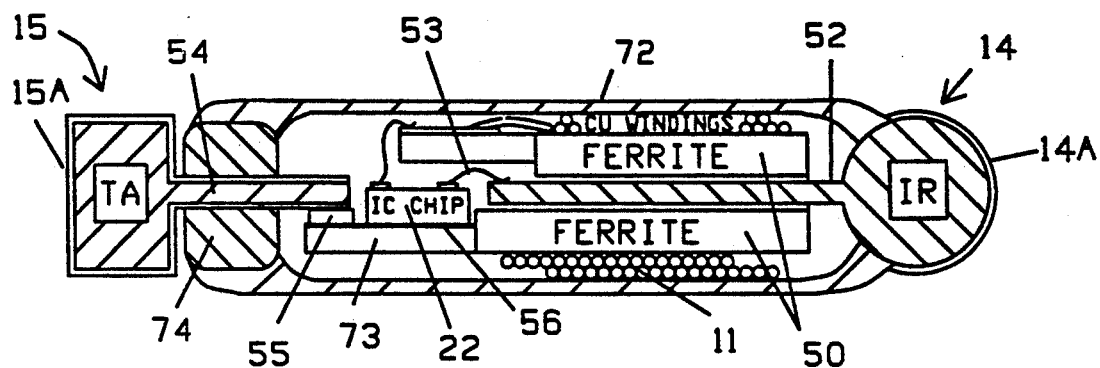
FIG. 8 is a cross-section side view of a microstimulator.

Electrode 15, in one embodiment, would be placed at the opposite end of the microstimulator from electrode 14, FIG. 8, and is comprised of anodized, sintered tantalum, and has a stem extending into the microstimulator. A substantial portion of the tantalum electrode would also be exposed outside the stimulator.

Electrode 15 is sintered, anodized tantalum which allows intimate relationship with the body fluids, but is of sufficiently small cellular structure that fibrous growth does not occur within the cells. Such tantalum electrode 15 and the counterelectrode of iridium 14 provides, by their structure, an electrolytic capacitor, shown as capacitor 20, with resistance 21 illustrating the resistance of the path through the body, approximately 300 ohms, between the electrodes. The capacitance provided by electrolytic capacitor 20 is significant, being on the order of 2 to 30 microfarads. It has been found by others that anodized tantalum has a very low DC leakage level when biased up to 80% of its anodization voltage and tends to self-heal in body fluids.

Figure 14:
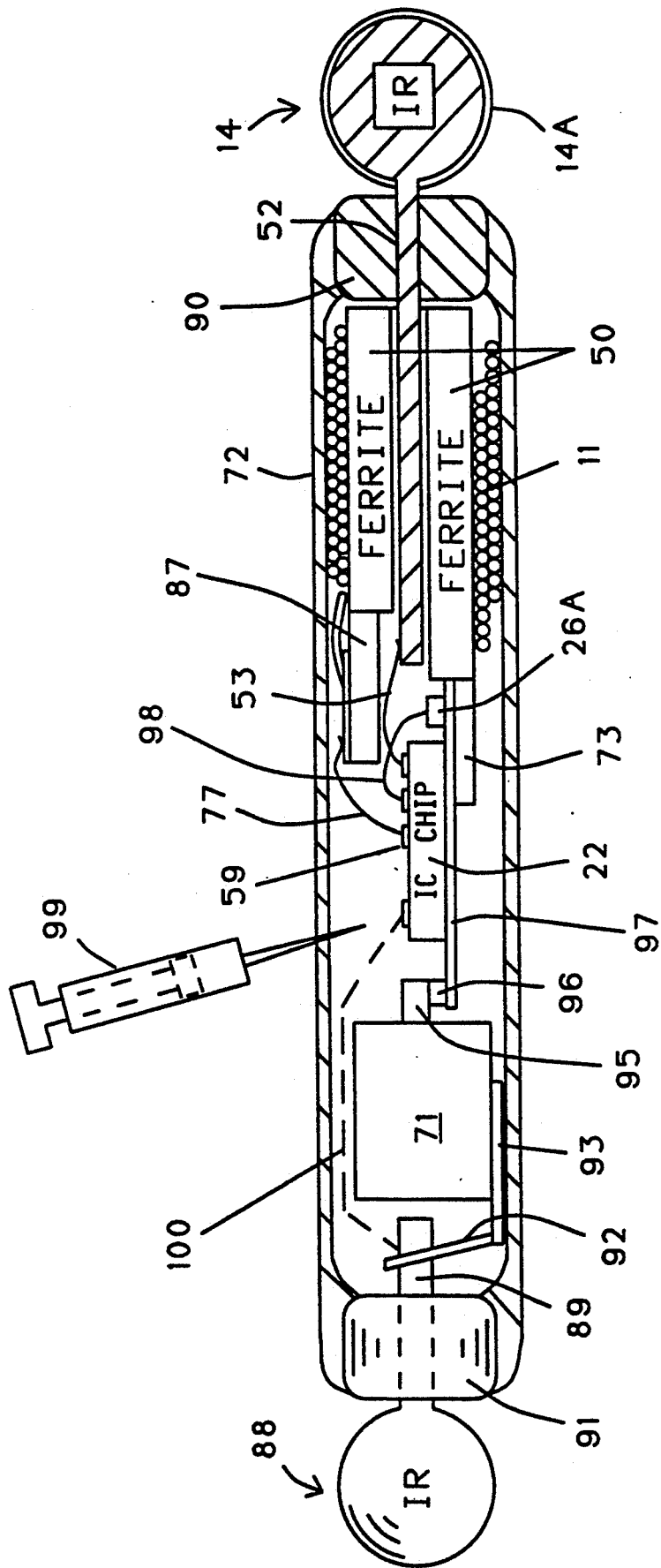
FIG. 14 is an alternate embodiment having an iridium electrode at each end of the microstimulator and an electrolytic capacitor disposed within the housing of the microstimulator.

In a preferred embodiment, the electrode 15 is not tantalum, but is an iridium spherical electrode 88, as shown in FIG. 14, similar to iridium electrode 14. In still other embodiments such electrode 88 may be merely a pellet or wire of pure tantalum, iridium, platinum, platinized metal, or suitable biomedical alloys of such metals. The capacitance is then provided by an internal capacitor in series circuit such electrode, as shown by electrolytic capacitor 71 in FIG. 3 and a capacitor or capacitors such as shown at 82 in FIG. 12 which will be discussed hereafter. Such discrete capacitor, however, occupies a substantial amount of space within the microstimulator, in order to achieve the desired amount of capacitance. The capacitor is preferably not constructed within the electronic circuitry chip 22, but is, rather, a separate capacitor, as shown and discussed hereafter in connection with FIG. 14.

The electrodes 14 and 15 may be constructed of other suitable metals. Platinum or platinized wire, for example, may be used. A platinum wire may be used for electrical connection through the end of the microstimulator, with the housing fused, or otherwise sealed, thereto. A glass bead may be used on the platinum wire, to aid in sealing it to the housing, as described hereinafter with respect to the tantalum stem. See FIG. 8.

Further, electrodes of other shape, size and disposition may be used. Elongated electrodes, with or without anchors to hold them in place may be used. Two or more electrode wires may exit at one end, if disposed electrically independent of each other. Such disposition may be done by using a glass bead having two holes therethrough, much the same as a button, and threading a wire through each hole and fusing the glass to the wire and, subsequently fusing the glass to the housing. Such is further described in connection with FIG. 12.

The power supply portion of 12 provides voltage at two levels, for example, V+, 8 to 15 volts, unregulated, for providing stimulating pulse energy storage on the tantalum electrode and VL−, −2 to −4 volts, regulated, for power for digital logic 16. Such low voltage may also be achieved, by a tap on coil 11. A V+ voltage of 10 volts has been found to be suitable.

Figure 3:
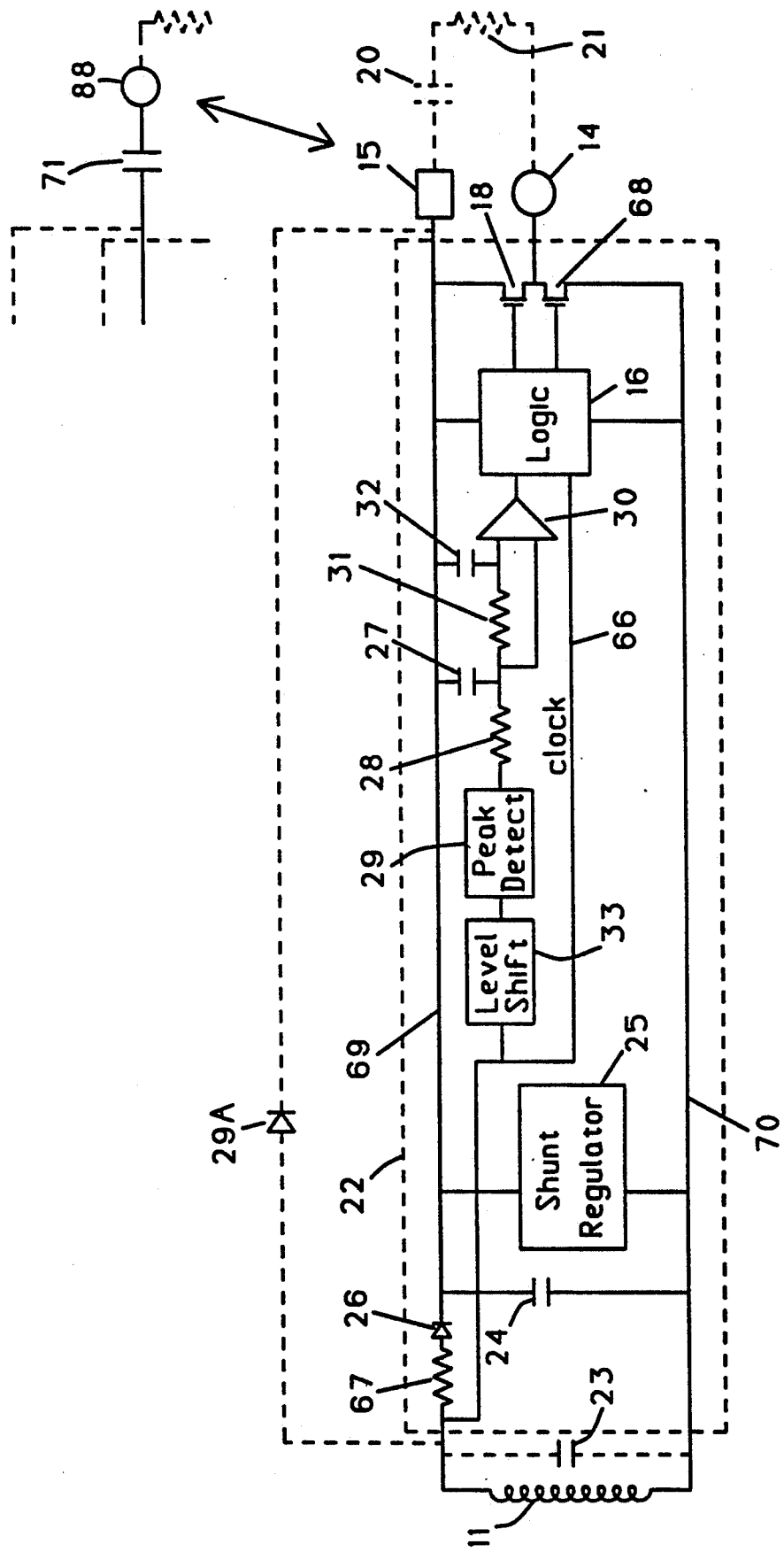
FIG. 3 is a simplified embodiment of the electrical circuit, including the electronic control means, of an implanted microstimulator.

Data detector 12 also provides clock and digital data information to logic 16 which decodes the control information contained within the modulated, alternating magnetic field. Such decoded information is used by the logic 16 to control switch 17 which controls the charge build-up between electrode 14 and electrode 15. Logic 16, which is preferably high speed, low current, silicon-gate CMOS, controls switch 18 (which may be a transistor, as shown in FIG. 3) which permits the stimulating pulse current to flow between electrodes 14 and 15. Logic 16 also controls current amplitude buffer 19. This controls the amount of current allowed to flow in each pulse.

Thus, all of the elements to receive, detect and store modulated, electrical energy and to decode and use the modulating information to cause the desired stimulating pulses, is provided by the microstimulator. Such elements are all within the microstimulator except for the exposed electrodes and, in the preferred embodiment, the storage capacitor for the stimulating pulses. Such storage capacitor 20, FIG. 2, is provided by tantalum electrode 15 together with iridium counter electrode 14, extending beyond the microstimulator and thus immersed in body fluids.

Such electrode 15, although it may only be 1.5 mm on a side, will easily store 100 microcoulombs of charge. Only 3.84 microcoulombs of charge is required for a 15 ma stimulating pulse having a 256 microsecond duration. Furthermore, the charge may be stored at a voltage (say, 10 volts) sufficient to overcome the output impedance (approximately 300 ohms) of the two electrodes and the intervening tissues of the body. Upon the largest stimulation pulse, the voltage between the electrodes 14 and 15 may drop to 8 volts, for example.

FIG. 3 is a simplified embodiment of the electrical circuit of the microstimulator. It shows power rectification and signal detection in more detail than that shown in FIG. 2. Most of the electrical circuit of the microstimulator is contained on an integrated circuit, or microcircuit, chip 22.

The coil 11 is tuned by capacitor 23 to the frequency of the alternating magnetic field. In some instances, capacitor 23 may be provided by the stray capacitance of coil 11. Resistor 67 and Schottky diode 26 provide rectification and a power bus 69 for the positive side of the received electrical energy. If it is desired, an external diode, such as that shown at 26A may be utilized. It is connected around microcircuit chip 22, from one end of coil 11 to the external connection of the electrode 15.

This external diode 26A is particularly useful in the event the chip diode 26 fails or does not meet the product specification or would otherwise prevent the electronic chip 22 from being usable or acceptable. The physical disposition of such diode 26A is better shown in FIG. 14. In FIG. 3, capacitor 24 serves to smooth out the ripple in the power bus 69. Shunt regulator 25 serves as a current shunt to prevent the voltage between the positive and negative power busses 69 and 70 (and thus between the electrodes 15 and 14) from becoming too high, say, above 15 volts. Shunt regulator 25 may be comprised of one or more Zener diodes and resistors or more sophisticated voltage regulating circuitry. The shunt regulator 25 effectively controls the excess energy which is received by dissipating it at an acceptable rate. It is expected that dissipation would not exceed approximately 4 milliwatts/cm$^2$, which is about 20% of levels which have been found acceptable in cardiac pacemaker dissipation.

Another method of Controlling the amount of energy received and stored by the microstimulator would be by connecting a voltage regulator in place of regulator 25, to switch a capacitor in and out of circuit in parallel with capacitor 23. FIG. 11, discussed hereafter, illustrates such a voltage regulator 80 connected across voltage bus lines 69 and 70 and controlling transistor 79 which switches capacitor 78 in and out of the receiving circuit comprising coil 11. In this manner, the amount of electrical energy stored in the capacitor means is controlled.

It is pointed out that lowering the Q of the power supply and the receiving circuit, by a shunt-regulator which dissipates energy or provides a current-sinking path, effectively stabilizes the electronic control circuit, particularly the demodulator and detector so that variations in loading do not interfere with signal demodulation or detection. At the same time, the shunt-regulator, or current-sinking means, prevents overcharging or overloading the storage capacitor means in the microstimulator.

Level shift 33 is connected to receive the energy received by the receiving coil 11 and drops the peaks to a detection range so the peak detector 29 can detect the peaks. From that detected signal, a short term detected signal is obtained by capacitor 27 and resistor 28 and a long term average detected signal is obtained by capacitor 32 and resistor 31 (which have a longer time constant than the first resistor and capacitor). The short term detected signal and the long term average detected signal are fed into comparator 30 which provides the detected data to be processed by the logic 16. Such logic controls the stimulation transistor 18 and the recharge transistor 68. When transistor 18 is conducting, transistor 68 is non-conducting and the charge between electrodes 14 and 15 is used to provide a stimulating pulse. In the preferred embodiment only a small part of the charge between the electrodes is utilized in the stimulating pulse.

Logic 16, would not require the full voltage of the V+ between lines 69 and 70, and may be operated on 2 to 4 volts, by a series regulator, (not shown) which would reduce and control the supply voltage to logic 16.

In order to restore the full charge between electrodes 14 and 15, or, in other words, the charge on the capacitor 20, transistor 18 is controlled to be non-conducting and transistor 68 is controlled to be conducting and the voltage busses 69 and 70 charge up the electrodes.

If the microstimulator does not use anodized, porous tantalum or other structure which provides an electrolytic capacitor when disposed in the body fluids, then a miniature capacitor may be required to be disposed inside the housing of the microstimulator. Such a capacitor is shown as capacitor 71 or as capacitor 82 in FIG. 12. Such capacitor may be manufactured on the electronic chip 22, but is preferably external to the electronic chip 22, as shown by capacitor 82, one of three, for example, in FIG. 12. An electrolytic capacitor 82, having 10 or 15 microfarads, would be typical.

Figure 4:
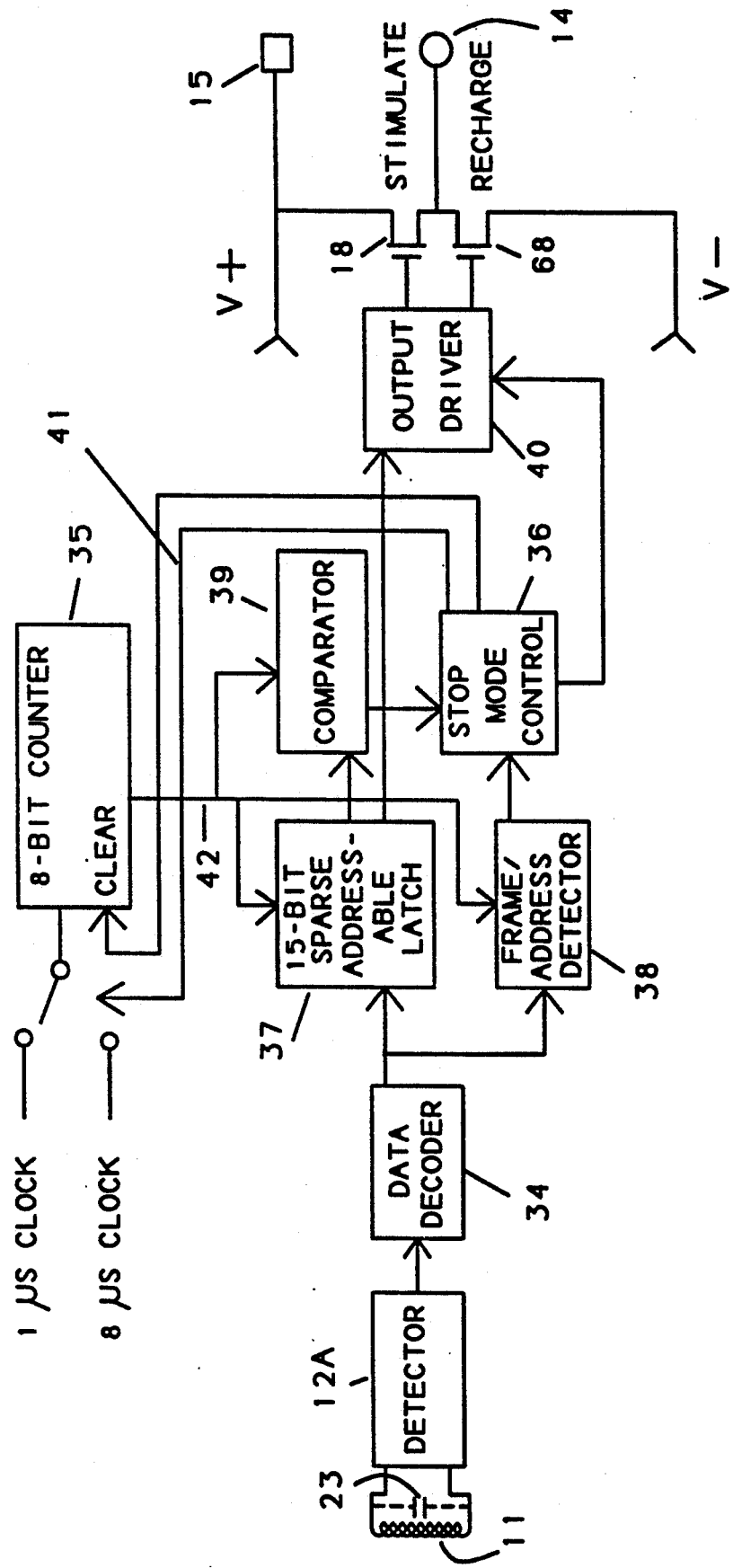
FIG. 4 is a block diagram of the electronic control means of the implanted microstimulator.

FIG. 4 is a block diagram illustrating one implementation of the circuitry of the electronic control means of the microstimulator. Assuming a 2 mHz, modulated, alternating magnetic field is transmitted from outside the skin, coil 11 and capacitor 23 provide the signal at that frequency to data detector 12A, (part of power supply and data detector 12, FIG. 2). Assuming that the modulating information is contained in 36-bit frames, data detector 12A provides such 36-bit frame data to data decoder 34.

Data decoder 34 sends the data, to 15-bit sparse addressable latch 37 and the frame/address detector 38. Latch 37 is essentially a CMOS RAM storage device which stores only a portion of the received frame, in this instance, pulse duration and pulse amplitude. Location within a frame of data is signaled by the 8-bit counter 35 on line 42 to latch 37, frame/address detector 38 and comparator 39.

Latch 37 captures only those 15 bits relating to pulse width, pulse amplitude, range, recharge level and shape, (pulse tail or not), within a 36-bit frame, which is discussed in more detail hereafter. The latch 37 may be much like a CMOS static RAM with 6 transistors per storage cell.

Frame/address detector 38 looks at an incoming frame bit by bit and determines whether the information is addressed to this microstimulator. It also checks the validity of the entire frame, which may be parity-encoded to insure accuracy. In the preferred embodiment, Manchester encoding of the bit transmission is also used.

A frequency source (not shown) provides one or the other of two clock signals to 8-bit up counter 35, under the control of mode control 36. Such clock signals may be asynchronous with the 2 mHz frequency received from outside the skin. In the preferred embodiment, however, the clock signals are synchronous with the frequency of the received alternating magnetic field, by being derived from the received signal. This would be accomplished by clock signals which are obtained synchronously from the data decoder 34, from the alternating magnetic field frequency. As shown in FIG. 4, the asynchronous version, one clock signal is a 1 microsecond per count clock signal used in controlling the duration of the stimulating pulse and the other is an 8 microseconds per count clock signal used in developing and validating the data being received. Thus, the mode control 36 calls for one or the other of two modes, one mode, "generate pulse" ( the 1 microsecond per count mode) and the other mode, "search for valid frame", (the 8 microsecond per count mode). Mode control 36, by controlling line 41, controls the input to 8-bit counter 35 and determines which count mode, 1 microsecond per count or 8 microseconds per count, is being received by the counter 35 from the frequency source.

During the 8 microsecond mode, if a valid 36-bit frame is not received by frame/address detector 38, or the address is not to this stimulator, the detector 38 resets itself, notifies mode control 36 which resets the 8-bit counter to zero and the search for a valid frame having a correct address commences again. If a valid 36-bit frame is received by detector 38, it notifies mode control 40 which switches to "generate pulse" mode, by clearing the 8-bit counter 35 and switching counter 35 to receive the 1 microsecond per count. The output driver 40 controls transistor 18 which is turned on to allow a stimulating pulse for the requisite time as determined when comparator 39 determines that the count, from 8-bit counter 35, is equal to the stored count in latch 37. When such counts are equal, comparator 39 advises mode control 36 (that the pulse has been on the required time) and to stop. Mode control 36 then stops driver 40 which turns off transistor 18, so that it is non-conducting. While transistor 18 is turned on, of course, tantalum electrode 15 and iridium electrode 14 are discharging a portion of the electrical charge between them, on capacitor 20, FIG. 3, thus providing a stimulating pulse through the body.

Transistor 68 is controlled by output driver 40 to restore the full charge on tantalum electrode 15 with respect to iridium electrode 14, in preparation for the next stimulating pulse. The recharge current is 100 microamps, in high recharge, and 10 microamps, in low recharge. The stimulating pulse amplitude may be, for example, 2 to 30 ma, in the high stimulation range, and 0.1 to 1.5 ma in the low stimulation range.

Figure 5:
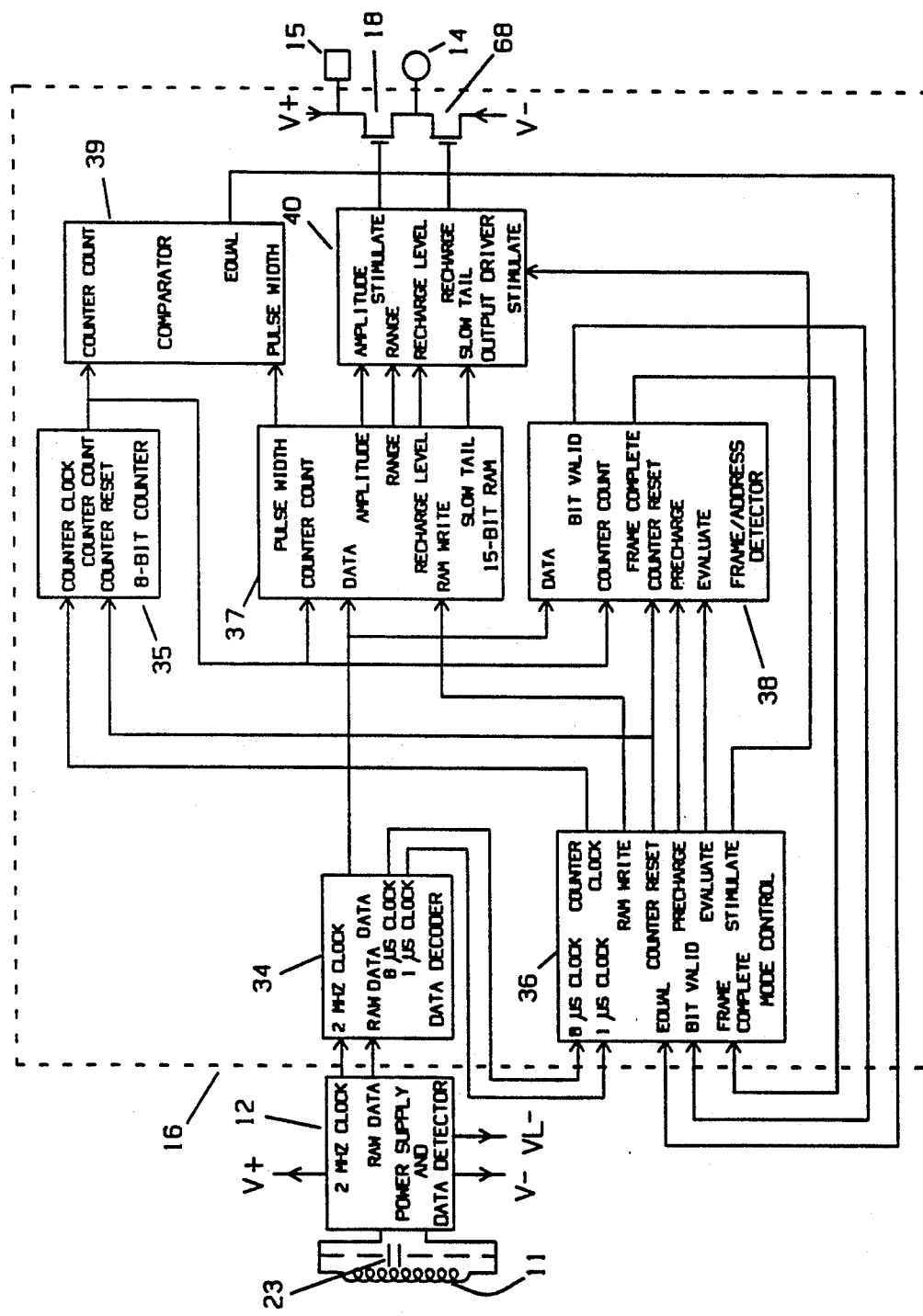
FIG. 5 is a block diagram showing the flow of data and clock information in a slightly different embodiment than FIG. 4.

FIG. 5 is another embodiment of the microstimulator, showing more detail as to the flow of data and clock information, than is shown in FIG. 4. The induced modulated, alternating magnetic field is received by coil 11 and capacitor 23 and is transmitted, as discussed with reference to and illustrated in FIG. 2, to power supply and detector 12, which provides a 2 mHz clock (from the received 2 mHz signal) and the raw data to data decoder 34, inside logic 16, shown in dotted lines. Both the power supply and data detector 12 and the logic 16 are included on the same integrated circuit chip 22 discussed hereafter in connection with FIGS. 8 and 9.

Data decoder 34 develops a 1 microsecond per count and an 8 microsecond per count clock signals and send them to mode control 36. Data decoder 34 also sends the data to 15-bit RAM 37 and frame/address detector 38. The data written into 15-bit RAM is controlled by the mode controller 37, (after frame/address detector 38 has validated the frame of data to controller 37), which allows 15-bit RAM to store the data bits pertaining to stimulating pulse width, amplitude, pulse range, recharge level, and whether a pulse tail is to be provided.

Ram 37 stores received data directing the amplitude of current in the stimulating pulses. In a preferred embodiment, two ranges of current are selectable, one range, 0.1 to 1.5 mA, and the other range, 2 to 30 mA. Ram 37 sends the range signal to output driver 40, together with signals as to amplitude within such range, the recharge level (high and low levels of recharge are allowed, say, 100 microamperes and 10 microamperes, respectively), and whether a pulse tail is desired on the stimulating pulse. Driver 40 carries out such information by control of stimulating transistor switch 18 and recharge transistor switch 68.

A pulse tail an exponential tail, (or a "ramp", as termed in FIG. 7) on a stimulating pulse provides a capability of controlling the direction of stimulation pulse flow along a nerve. Work at Case Western Reserve by Fang and Mortimer has determined that a pulse-tail will achieve anodal block of large diameter axons in nerve cuff applications. A tail of 300 microseconds is suggested by that work.

As in FIG. 4, frame/address decoder 38, validates or invalidates the received frame of data and notifies mode control 36. If the frame is invalid, both the counter 35 and detector 38 are reset by mode control 36 to commence again.

As in FIG. 4, comparator 39 compares the count from 8-bit counter 35 and 15-bit RAM 37 and indicates to mode control 36 when the stimulating pulse duration (width) is equal to that ordered by the received data stored in RAM 37. Upon it becoming equal, mode control 36 ceases advising output driver 40 to stimulate.

A particular feature is desirably included in detector 12. If the received power drops to less than 5 volts, or if there is no carrier or loss of carrier, the detector 12 shuts down all parts of the system by a reset signal. Also, mode control 36 will not send out any signal to the output driver 40 to generate a stimulating pulse, until the received address and control information have been validated. Thus, undesired stimulation does not take place during initial charge-up of the storage capacitor means, or during intervals of low or incorrect induced voltages or control signals.

Mode control 36 is also preprogrammed to provide a predetermined, initial, pull-up of the CMOS circuitry (by the precharge signal to the frame/address detector 38). Implementing the CMOS with an initial pull-up and then pull-down upon receipt of validated signals, simplifies the logic.

Further, such mode control 36 maintains control and does not direct stimulation until successful, valid address bits and control bits are received and so indicated by the frame/address detector 38.

Figure 6:
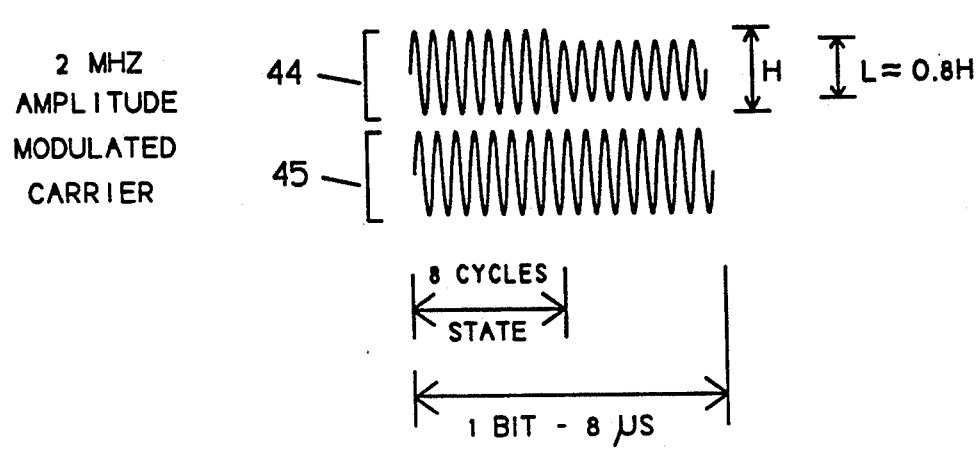
FIG. 6 illustrates the encoding of "1's" and "0's" in the transmission of control information, within the alternating magnetic field transmitted to the microstimulator.

FIG. 6 shows one method of using amplitude modulation of the oscillator 6, FIG. 2, to carry the control information being sent to the microstimulator from outside the skin. The encoding uses 16 cycles of the 2 mHz carrier, at its full, received amplitude, as a logical "0" and 8 cycles at the full, received amplitude plus 8 cycles of reduced amplitude, as a logical "1", as illustrated in FIG. 6. FIG. 6 illustrates the reduced amplitude as being 0.8 the height of the full amplitude of the received wave. Waveform 44 represents a logical "1" and waveform 45 represents a logical "0".

In FIG. 6, it may be seen that 16 cycles of the 2 mHz amplitude modulated carrier would provide an 8 microsecond wide bit. Clock pulses of 1 microsecond (2 cycles of the 2 mMz carrier) and 8 microseconds (16 cycles of the 2 mHz carrier) are readily generated for timing within the microstimulator as discussed hereinafter.

Figure 7:
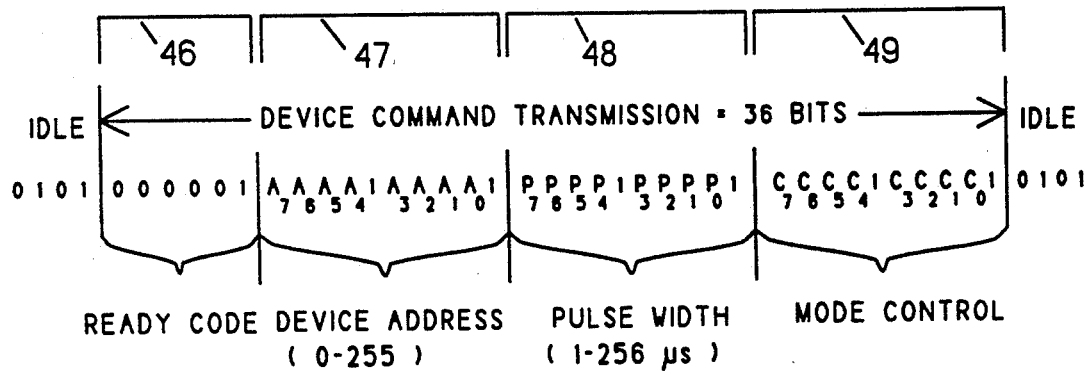
FIG. 7 illustrates one manner of encoding the control information within a frame of date transmitted to the microstimulator.

FIG. 7 illustrates one manner of encoding a frame of data, of "1's" and "0's" within the alternating magnetic wave, to carry the control information. Using an information frame 36-bits long, the information is encoded and transmitted to the microstimulator.

As shown in FIG. 7, the first six bits 46 comprises five "0's" followed by a "1" to indicate the start of the frame. Therefore, the first six bits 46 indicates "start" or "get ready". The next eight bits 47 contain the address of the device being addressed. Consequently, 256 devices may be individually addressed. The next eight bits 48 contain information pertaining to the pulse width, say, from 1 to 256 microseconds. The last set of eight bits 49 contains further information to control the pulse.

In the example shown, four of the last eight bits, $C_{7-4}$ contain the current amplitude values (say, 0-15 steps). The next bit, $C_3$, contains the range of current amplitude (say, 0.1 to 1.5 ma or 2 to 30 ma). The next bit, $C_2$, whether the stimulating pulse is square or has a pulse tail (called a "ramp" in the drawing). The next bit, $C_1$, sets the current recharge value (10 or 100 microamperes), and the final bit, $C_0$, is encoded as a parity bit, for error checking.

Thus, the stimulating pulse is controlled as to when it should exist, its duration (width), its range of amplitude and specific amplitude in that range, its shape, and the recharge current to get ready for the next stimulating pulse.

Idle pulses of "0's" followed by "1's" may be sent as shown in FIG. 7, before and after each frame of data.

Manchester encoding may be used to assure reliability. In such encoding, there is always a transition, from high to low or vice versa, at the end of sixteen cycles, which is the bit time. See FIG. 6. If there is a transition at 8 cycles, the state time, the bit may be termed a "1". If there is no transition at 8 cycles, the bit is then a "0".

Control of additional microstimulator capabilities may be added by extending the information frame of data to more than 36 bits.

FIG. 8 is a cross-section side view of a microstimulator. The iridium electrode 14 and the tantalum electrode 15 are at opposite ends of the microstimulator. The anodized layer 15A on tantalum electrode 15 and the activated layer 14A on iridium electrode 14 provide a substantial capacitance between them when the microstimulator is implanted and the porous tantalum and, thus, the iridium ball are immersed in body fluids.

In the manufacturing process, the exposed surface of electrode 14 is activated by immersing it in a phosphate-buffered saline solution and touching its outside surface with a whisker probe, (fine iridium wire of 0.003" D), and cycling for 20 to 30 minutes at 0.5 volts per second to a maximum of plus or minus 0.8 volts. The cyclic voltammetry builds up an electrically conductive layer of iridium hydrous oxide, layer 14A, (an activated layer), that is capable of being cycled reversibly between the +3 and +4 valence states, thereby transforming electron motion in the underlying metal into ion fluxes in the surrounding solution without inducing irreversible electrolysis of the water or metal. The interfacial impedance tends to be very low, also, reducing the necessary voltage between the electrodes 14 and 15 to be used in obtaining stimulation.

The coil 11 is shown wound around a ferrite core 50. Such core is cylindrical and is manufactured in two halves with a U-channel in each one. When such halves are placed together, a channel is thus formed between them. The iridium stem 52 passes through such channel. Integrated circuit chip 22 is carried on a ferrite shelf 73 and is connected to receive the output of the coil 11. Iridium electrode 14 is connected through its stem 52 and wire 53 to receive the output of chip 22 and be controlled thereby. Tantalum electrode 15 is connected through its stem 54 and through weld shim 55 to a metallized pad 56 on the shelf 73 of ferrite 50. Integrated circuit chip 22 sits on metallized pad 56 and is thus connected through its base, or substrate, to stem 54 of electrode 15. Thus, electrodes 14 and 15 are both connected to receive the output of chip 22 and be controlled thereby. The integrated circuit chip 22, in a preferred embodiment, is double-poly, p-well (3 micron) CMOS in which the substrate is at the V+ supply rail to which the tantalum electrode may be readily connected.

In another embodiment, weld shim 55 and metallized pad 56 are replaced by a small metallized pad on ferrite shelf 73 to which both the tantalum stem 54 and integrated circuit chip 22 are electrically connected, by flying bond wires or other means.

It is noted that such electrodes, or their leads, are hermetically sealed to housing 72. The preferred embodiment comprises a housing of N51A glass or other suitable biomedical grade capillary tubing having an inner diameter of about 1.25 mm's. It is available from or through glass fabrication houses such as Kimbel Glass, Corning Glass and others.

It is important to select a glass which is stable in body fluids and which matches pretty well the coefficient of thermal expansion of the tantalum and iridium because of the heating operations involved in fusing the electrodes to the glass housing.

In the case of the tantalum electrode 15, the stem 54 is first fused to glass bead, or washer, 74, and then the glass bead 74 is fused to the housing 72. In the case of the iridium electrode 14, the ball portion provides a good sealing surface and is fused directly to the housing 72. In alternate embodiments, a simple platinum or titanium wire, or wire of other suitable metal, may pass through the end of such microstimulator and be fused to the housing 72 to provide a hermetic seal. External electrodes may be constructed on otherwise attached to such wires, as desired, or such wires may, themselves, be the electrodes.

Figure 9:
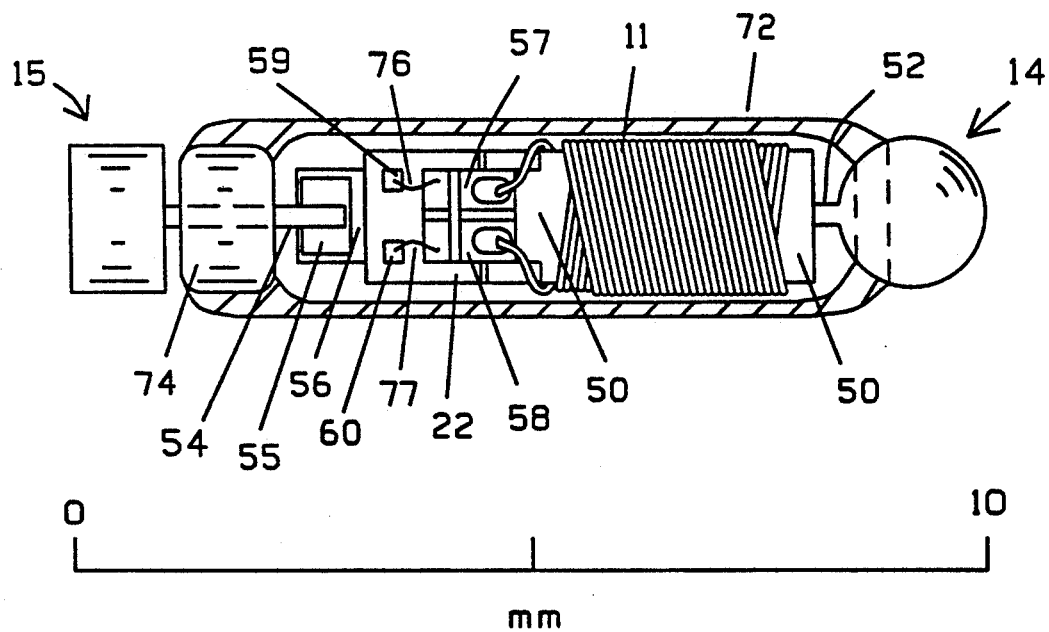
FIG. 9 is a top view of a microstimulator with the housing in cross-section.

FIG. 9 is a top view of a microstimulator with only the housing 72 shown in cross-section. Coil 11 is illustrated as being numerous turns of a fine wire and is included within the microstimulator housing 72 which is only approximately 10 mm long. The coil 11 and ferrite core 50 occupy a large part of the housing 72. Coil 11 may be approximately 200 turns or more of a fine, copper wire. The coil 11 acts as the secondary of a transformer and receives energy by induction from outside the body.

A preferred embodiment in the construction of coil 11, is 250 turns of 0.00102" D, or finer, insulated, copper wire on a ferrite core having a diameter of approximately 0.050". Due to the stray, or distributed capacitance of such windings, the coil would be resonant at approximately 2 mHz.

In FIG. 9, the two ends of the coil 11 are shown connected to two metal pads 57 and 58, which may be made, for example, of palladium-silver disposed on a ferrite shelf 87, shown in FIG. 8. Such pads 57 and 58, in FIG. 9, are further connected to provide input to the integrated circuit chip 22 by means of gold bonding wires 76 and 77 being connected to pads 59 and 60. The integrated circuit chip 22, in turn, provides a controlling output to the two electrodes 14 and 15, as explained previously in connection with FIG. 8.

FIG. 10 shows a 2 mHz oscillator 61 receiving modulation and driving external transmitter coil 1, which provides an alternating magnetic field modulated in accordance with desired information. Coil 11 is adapted to receive the alternating magnetic field through skin 8. Suitable transmitters and receivers are well-known in the art. Class E drivers, which are highly efficient if properly modulated and operated, are particularly suited to drive coil 1. Such class E drivers are well-known in the art and an analysis may be found in an article entitled, "*Exact Analysis of Class E tuned Power*

*Amplifier at any Q and Switch Duty Cycle,"* Kazimierczuk and Puczko, IEEE Transactions on Circuits and Systems, Vol. CAS-34, No. 2 February, 1987, pp. 149-159. Numerous additional references discussing class E drivers and amplifiers which may be used as drivers are therein cited. Inductive transdermal links are further disclosed and discussed in U.S. Pat. No. 4,679,560, for Wide Band Inductive Transdermal Power and Data Link, inventor, Douglas C. Galbraith and in *"RF Powering of Millimeter- and Submillimeter-Sized Neural Prosthetic Implants,"*, William J. Heetderks, IEEE Transactions on Biomedical Engineering, Vol. 35, No. 5, May, 1988.

FIG. 11 illustrates another means of controlling the amount of energy stored by the microstimulator. The method of controlling the amount of energy stored is to control the amount received by the coil 11. If it is de-tuned from the resonant frequency, by varying the capacitance in circuit with it, it will not receive so much energy. Coil il and capacitor 23 form a circuit tuned to the frequency of the signal being transmitted by the transmitter outside the skin. Capacitor 78 and transistor switch 79 are connected across coil 11. Voltage regulator 80 is connected to receive the rectified and smoothed voltage across bus lines 69 and 70 and provides a control of switch 79. When the voltage build-up is too high across bus lines 69 and 70, transistor switch 79 completes the circuit and capacitor 78 is switched into circuit with coil 11. The circuit comprising coil 11 is then de-tuned from the transmitting frequency and receives less power than when tuned to the transmitting frequency. As soon as the bus voltage drops, voltage regulator 80 opens transistor switch 79 and the coil 11 is again in a circuit tuned to the transmitting frequency.

Figure 12:
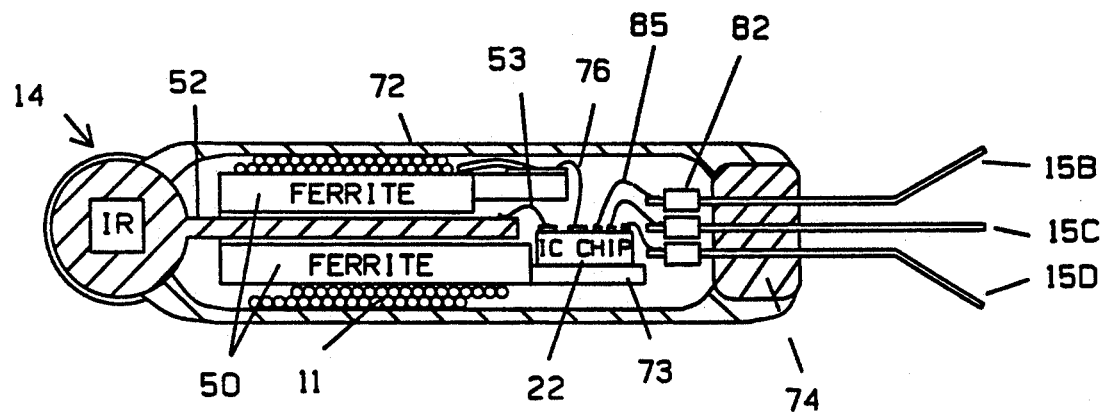
FIG. 12 is an alternate embodiment showing multiple electrodes and storage capacitors in one end of the microstimulator.

FIG. 12 illustrates multiple electrodes 15B, 15C, and 15D in place of the single tantalum electrode 15 illustrated in FIGS. 8 and 9. Such electrodes in FIG. 12 may be platinum, platinized wire, tantalum, iridium, or other suitable biocompatible, metal. They appear to be of the same metal, but of course, each electrode may be different than the others. Also, they may be of other shapes than the simple wire shape shown in FIG. 12. In this embodiment, the electrodes do not provide an electrolytic capacitance by being immersed in body fluids, but, rather are each connected in series with an axial capacitor, such as axial capacitor 82. Such capacitors may be electrolytic, tantalum capacitors, or other capacitors readily available from manufacturers. The capacitors are, in turn, connected to individual connection pads on electronic circuitry chip 22 by flying bond wires such as wire 85.

Figure 13:
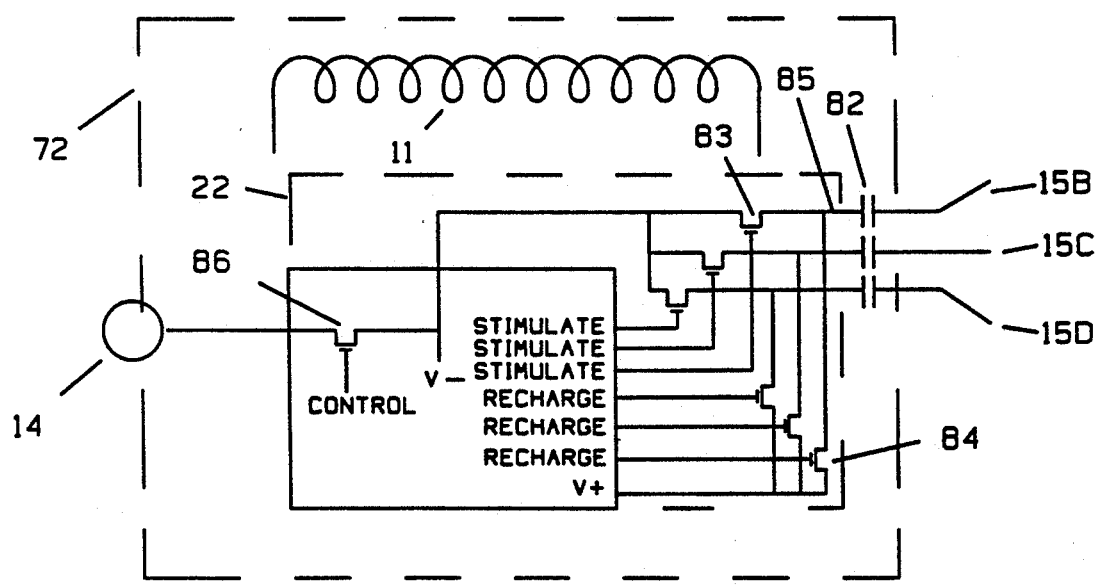
FIG. 13 illustrates the electrical control of multiple electrodes and individual storage capacitors.

In FIG. 13, it may be seen that the charge build-up on such capacitors is controlled by control circuitry on the electronic circuitry chip 22 which controls transistor switches such as switch 84 which connects the storage capacitor of each electrode to the V+supply. In order to complete the charging circuit, transistor switch 86, in circuit with electrode 14 must be closed, connecting the counterelectrode 14 to the V— supply. The charging circuit is thus completed through the body fluids and tissue and a charge is stored on the axial capacitors of each electrode, such as capacitor 82. The electrodes 15B, 15C and 15D are shown as having individual capacitors and switching transistors, but they may, of course, have a single capacitor and switching transistor, driving them all.

For stimulation, which discharges, or partly discharges the axial capacitors, the transistors such as transistor 83 are closed, together with transistor 86, thus connecting the electrodes 15B, 15C and 15D in circuit with counterelectrode 14 to provide stimulation pulses, provided by the charge on the axial capacitors, to the body tissue and fluids. Control of such transistor switches to control pulse timing, duration, amplitude and shape, utilizes the same concepts previously discussed in connection with FIGS. 8 and 9, in connection with a single tantalum electrode.

The embodiment shown in FIGS. 12 and 13 allows the provision of a single large stimulating pulse, or quick, successive pulses, or spaced pulses at rates and magnitudes not otherwise achievable. Such wire electrodes may be longer than the proportions shown in the drawings. The technique for using a hypodermic syringe for implanting the electrodes in the body permits the expulsion of the microstimulator by withdrawing the syringe as the microstimulator is expelled, thus leaving the microstimulator and its electrodes in place. A microstimulator having a long electrode or long electrodes could thus easily be implanted by a syringe.

Transistor 86 is not necessary in some instances and the iridium electrode 14 is connected directly to the V— power supply bus. However, transistor 86 can be used to effectively isolate iridium electrode 14 from the power supply and other circuitry within the system.

Coil 11 is shown figuratively in FIG. 13, unconnected, but would, of course, be connected as shown in FIGS. 3 and 9. Coil 11, of course, is connected to electronic circuitry chip 22, as shown in FIG. 9, by bond wires 76 and 77. One of such wire connections, wire 76 is shown in FIG. 12.

Axial capacitors need not be used, but other shapes may be utilized. Referring to FIG. 8, for example, a capacitor, or multiple capacitors, may be located in the electrical circuit and at the place occupied by weld shim 55. It may be seen that one side of the capacitor would be connected to the tantalum electrode, as shown in FIG. 8, and the other side, to the electronic circuitry chip 22 through metallized pad 56.

FIG. 14 illustrates a preferred embodiment in which iridium electrodes 14 and 88 are disposed at opposite ends of the microstimulator. Electrode stems 52 and 89 pass through glass beads 90 and 91, respectively. Such construction allows for assembling the microstimulator by threading the electrode stems 52 and 89 through glass beads 90 and 91, fusing each glass bead to its respective stem, then fusing the glass beads to the housing 72, when the glass beads and the internal assembly are suitably positioned in the housing.

Iridium electrode 88 is connected through its electrode stem 89 and a welded, soldered, or otherwise connected wire 92 to a metal plate, or to metallization 93, which is further connected to the one electrode, of electrolytic capacitor 71. In FIG. 14, such one electrode is the outer surface, or case, of the capacitor 71. Electrolytic capacitor 71 is further connected through its other electrode 95, to metal shim 96 and metal plate 97, to the base of electronic circuitry, IC chip 22.

An additional electrical connection 100, may be made from the other side of the electrolytic capacitor 93 to electronic chip 22, to provide electrical energy directly from electrolytic capacitor 71 to electronic chip 22.

It has been found that in such miniature construction, ferrite shelf 73 is prone to be broken. Making shelf 73 relatively short and adhering a longer metal plate 97 thereto provides sufficient area to mount electronic chip 22, shim 96 and diode 26A. The plate may be made of most any inert metal or metal alloy. Nickel and nickel alloy are particularly suitable. Flying bond wires, such as are shown at 77, 53, and 98, make desired electrical connections to the electronic chip 22.

The microstimulator may be assembled by assembling the internal structure, with electrodes at each end, and sliding such assembly through the housing 72 until the assembly is in place, with an iridium electrode extending out each end of the housing. The glass beads 91 and 52, which have previously been fused to the stems 52 and 89, are then fused to the housing 72. The housing may be filled with an inert material impervious to water, such as epoxy or silicon rubber through a hole in the housing by means of a syringe 99. The filling with epoxy, silicon rubber or other suitable inert material, may occur while the assembly is being placed within the housing or thereafter. Any holes or vents for filling the housing may be sealed up with the inert material or sealed by other means.

Inasmuch as the electronic chip 22 is light sensitive, a light barrier must be provided. Such light barrier may be a film or mask placed on the chip, an opaque or colored material used to fill the microstimulator, or a housing which is opaque or colored so as to prevent undesired light from reaching the chip 22.

Although specific embodiments and certain structural and electrical arrangements have been illustrated and described herein, it will be clear to those skilled in the art that various other modifications and embodiments may be made incorporating the spirit and scope of the underlying inventive concepts and that the same are not limited to the particular forms herein shown and described except insofar as determined by the scope of the appended claims.

We claim:

1. An implantable microstimulator substantially encapsulated within a hermetically-sealed housing which is inert to body fluids, said microstimulator comprising:
    a coil within said hermetically-sealed housing adapted to function as the secondary winding of a transformer, said coil adapted to e disposed in a modulated, alternating magnetic field,
    at least two exposed electrodes for providing electrical stimulation,
    electronic control means,
    capacitor means for storing power for said electrical stimulation, and for storing power for said electronic control means,
    means for controllably charging said capacitor means from said alternating magnetic field,
    said electronic control means controlling discharge of said capacitor means to provide electrical stimulation through said exposed electrodes and an electric path provided by a body wherein said microstimulator is implanted, and
    said electronic control means further providing control of at least one of the duration, the current and the shape of stimulus pulses that comprise said electrical stimulation in accordance with the modulation of said alternating magnetic field.

2. The microstimulator recited in claim 1 wherein is included means for controlling said microstimulator in the event of failure to receive sufficient power or invalid modulation, lack of sufficient modulation, and upon startup.

3. The microstimulator recited in claim 1 wherein said capacitor means is charged by a first electrical circuit using the body as part of the charging path and discharged, while said first electrical circuit is broken, by a second electrical circuit connecting said electrodes together inside said microstimulator.

4. The microstimulator recited in claim 1 wherein said means for controllably charging said capacitor means, comprises means for regulating the current flow in charging said capacitor means.

5. The microstimulator recited in claim 4 wherein said means for regulating the current flow, regulates said current flow below that which would stimulate said body area, have adverse effect on said body area and have adverse effect on said electrodes.

6. The microstimulator recited in claim 1 wherein said capacitor means is shunt-regulated at least in part to lower the Q of the power supply in aid of stabilization of said electronic control means.

7. The microstimulator recited in claim 1 wherein is included within said microstimulator, means for controlling the amount of electrical energy stored by said microstimulator.

8. The microstimulator recited in claim 7 wherein said amount of electrical energy stored by said microstimulator is several times the amount of electrical energy required by said microstimulator to stimulate.

9. The microstimulator recited in claim 7 wherein said means for controlling the amount of energy stored by said microstimulator comprises means for dissipating excess energy induced into said microstimulator.

10. The microstimulator recited in claim 9 wherein said means for dissipating excess energy comprises current-sinking means.

11. The microstimulator recited in claim 7 wherein said means for controlling the amount of energy stored by said microstimulator comprises a shunt regulator controlling the charging of said capacitor means.

12. The microstimulator recited in claim 7 wherein said means for controlling the amount of energy stored by said microstimulator comprises means for varying the resonant frequency of the electrical circuit comprising said coil.

13. The microstimulator recited in claim 1, wherein both of said electrodes are activated iridium.

14. The microstimulator recited in claim 1 wherein is also included means for preventing stimulation pulses upon failure of said microstimulator to receive sufficient induced power, for at least one of, proper stimulating pulses or control information.

15. The microstimulator recited in claim 1 wherein said electronic control means comprises detector means and decoding means receiving information from said modulated, alternating magnetic field, as to one or more of, stimulus pulse duration, stimulus pulse current, stimulus pulse shape and identifying the specific microstimulator, to which said modulated information is sent.

16. The microstimulator recited in claim 15 wherein said decoding means is synchronized with the frequency of said alternating magnetic field.

17. The microstimulator recited in claim 15 wherein said detector means comprises means for obtaining and comparing the short term signal and the long term average of such detected signal and providing the compared signal to said decoding means.

18. The microstimulator recited in claim 15 wherein is included means for providing control of one or more of the duration, the current and the shape of said stimulus pulses in accordance with the output of said detection and decoding means.

19. The microstimulator recited in claim 18 in which said microstimulator comprises means for providing stimulation and recharging in two substantially different ranges of current amplitude.

20. The microstimulator recited in claim 15 wherein is included means for storing the pulse control information received by said microstimulator, and where is included mode control means for controlling the storing of information in said means for storing in accordance with an evaluation of the address and validity of the received information.

21. The microstimulator recited in claim 1 wherein is included means to control said electrodes during the initial charge-up of said capacitor means for storing power and until valid control information is received.

22. The microstimulator recited in claim 1 wherein said microstimulator is of a size approximately 2 mm in diameter and 10 mm in length.

23. The microstimulator recited in claim 1 wherein is included means for controlling the amount of energy induced in said coil.

24. The microstimulator recited in claim 23 wherein said means for controlling energy induced in said coil comprises means for varying the capacitance in circuit with said coil, for detuning said tuned coil from said alternating magnetic field.

25. The microstimulator recited in claim 1 wherein said coil comprises 250 turns of 0.00102" D wire and said coil has a distributed capacitance which provides a resonant frequency of said coil at 2 mHz.

26. An implantable microstimulator substantially encapsulated within a hermetically-sealed housing inert to body fluids, said microstimulator being adapted to electrically stimulate living tissue of a body wherein said microstimulator is implanted, said microstimulator having means for receiving a modulated, alternating magnetic field providing power and information, stimulating circuit means comprising two electrodes and capacitor means for storing received electrical energy, said two electrodes adapted to be disposed in one or more of body tissue and connected in series circuit with said capacitor means for discharging said capacitor at least partially into said fluids and tissue, providing a stimulating pulse thereto, means responsive to modulations of said received energy to control the duration of said stimulating pulses to specific values within predetermined ranges and to control the current amplitude of said stimulating pulses to within specific values within predetermined ranges and means for providing a balancing current flow, between said two electrodes, between said stimulating pulses, in the opposite direction from said stimulating pulses.

27. The microstimulator recited in claim 26, wherein is included means for controlling the shape of said stimulating pulses.

28. The microstimulator recited in claim 27 in which said stimulation pulses are controlled to have either abrupt endings or endings with an exponential tail.

29. The microstimulator recited in claim 26 in which said means for providing a balancing, current flow comprises current-regulating means, preventing excess current flow in the direction opposite to said stimulating pulses.

30. The microstimulator recited in claim 26 in which said balancing, controlled current flow between said two electrodes maintains the voltage on the negative one of said electrodes at a voltage substantially below the potential causing cathodic depositions on said negative electrode.

31. The microstimulator recited in claim 26 in which said means for controlling pulse duration and said means for controlling pulse current each comprise further means for controlling said pulse duration and pulse current to low values as default upon one or more of startup of the system and lack of sufficient modulation information and lack of adequate received energy.

32. The microstimulator recited in claim 26 in which is included means for controlling said microstimulator upon one or more of lack of sufficient modulation of said alternating magnetic field and errors in said modulation.

33. An implantable microstimulator substantially encapsulated within a hermetically-sealed housing which is inert to body fluids, said microstimulator having a coil for receiving an alternating magnetic field, stimulating electrode means at one end and a counter electrode at the other end, capacitor means in circuit with said stimulating electrode means and means for controllably charging said capacitor means from voltage induced in said coil, means for at least partly discharging said capacitor means through said electrode means and said counter electrode into a body wherein said microstimulator is implanted and means for controllably recharging said capacitor means.

34. The microstimulator recited in claim 33 wherein said electrode means comprises a plurality of electrodes and said capacitor means comprises an plurality of capacitors, each disposed in circuit with a respective one of said plurality of electrodes and said means for controllably charging said capacitor means comprises means for individually charging said capacitors.

35. The microstimulator recited in claim 34 wherein said capacitors in circuit with said electrodes may be at least partly discharged, individually.

36. An implantable microstimulator having a housing, said microstimulator having inert, metallic electrode means comprising at least two electrodes electrically connected to the inside of said housing through a hermetic seal, one electrode being disposed at or near one end of said housing and the other electrode at or near the other end of said housing, electronic control circuitry and capacitor means disposed within said housing and connected between one of said electrodes and said electronic control circuitry, induction means comprising a coil for receiving a modulated, alternating magnetic field to provide power and control information for said microstimulator, said electronic control circuitry connected in circuit with said coil and said second electrode and providing control and electrical energy for the charge of said capacitor means and, at least partial discharge, of said capacitor means through said electrode means.

37. The microstimulator recited in claim 36 wherein said first electrode means comprises a plurality of electrodes.

38. The microstimulator recited in claim 37 wherein said capacitor means comprises a capacitor in series with each of said electrodes of said plurality of electrodes of said first electrode means.

39. The microstimulator recited in claim 38 wherein said electronic control circuitry comprises switches and regulator means for controlling the charge and at least partial discharge of electrical energy on said plurality of capacitors.

40. The microstimulator recited in claim 36 wherein said metallic electrode means comprises an iridium electrode disposed at each end of said microstimulator.

* * * * *